US010175192B2

(12) United States Patent
Afzali-Ardakani et al.

(10) Patent No.: US 10,175,192 B2
(45) Date of Patent: *Jan. 8, 2019

(54) SUPERHYDROPHOBIC ELECTRODE AND BIOSENSING DEVICE USING THE SAME

(71) Applicant: INTERNATIONAL BUSINESS MACHINES CORPORATION, Armonk, NY (US)

(72) Inventors: Ali Afzali-Ardakani, Ossining, NY (US); Karthik Balakrishnan, White Plains, NY (US); Stephen W. Bedell, Wappingers Falls, NY (US); Pouya Hashemi, White Plains, NY (US); Bahman Hekmatshoartabari, White Plains, NY (US); Alexander Reznicek, Troy, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,414

(22) Filed: Jun. 6, 2017

(65) Prior Publication Data

US 2018/0095053 A1 Apr. 5, 2018

Related U.S. Application Data

(63) Continuation of application No. 15/283,813, filed on Oct. 3, 2016, now Pat. No. 9,726,634.

(51) Int. Cl.
*G01N 27/414* (2006.01)
*G01N 27/30* (2006.01)
*H01L 29/417* (2006.01)
*H01L 29/06* (2006.01)
*H01L 29/20* (2006.01)
*H01L 29/16* (2006.01)
*G01N 27/327* (2006.01)

(52) U.S. Cl.
CPC ......... *G01N 27/4145* (2013.01); *G01N 27/30* (2013.01); *G01N 27/3278* (2013.01); *H01L 29/0684* (2013.01); *H01L 29/16* (2013.01); *H01L 29/20* (2013.01); *H01L 29/417* (2013.01)

(58) Field of Classification Search
None
See application file for complete search history.

(56) References Cited

U.S. PATENT DOCUMENTS 9,726,634 B1 * 8/2017 Afzali-Ardakani .................. G01N 27/4145

OTHER PUBLICATIONS

Ebrahimi et al., Nanotextured Superhydrophobic Electrodes enable Detection of attomolar-scale DNA concentration within a Droplet by non-Faradaic Impedance Spectroscopy, Nov. 7, 2013, NIH, 13(21), 4248-4256.*

(Continued)

*Primary Examiner* — Marcos D Pizarro
*Assistant Examiner* — Shannon Yi
(74) *Attorney, Agent, or Firm* — Tutunjian & Bitetto, P.C.; Erik Johnson

(57) ABSTRACT

A method for making a hydrophobic biosensing device includes forming alternating layers over a top and sides of a fin on a dielectric layer to form a stack of layers. The stack of layers are planarized to expose the top of the fin. The fin and every other layer are removed to form a cathode group of fins and an anode group of fins. A hydrophobic surface on the two groups of fins.

20 Claims, 8 Drawing Sheets

(56) References Cited

OTHER PUBLICATIONS

Ebrahimi, A. et al. "Nanotextured superhydrophobic electrodes enable detection of attomolar-scale DNA concentration within a droplet by non-faradaic impedance spscetroscopy" Lap Chip (Aug. 2013) pp. 4248-4256, vol. 13.
Melli, M. et al., "Fast Detection of Biomolecules in Diffusion-Limited Regime Using Micromechanical Pillars" ACS NANO (2011) pp. 7928-7935, vol. 5, No. 10.
List of IBM Patents or Patent Applications Treated as Related dated Jun. 6, 2017, 2 pages.

* cited by examiner

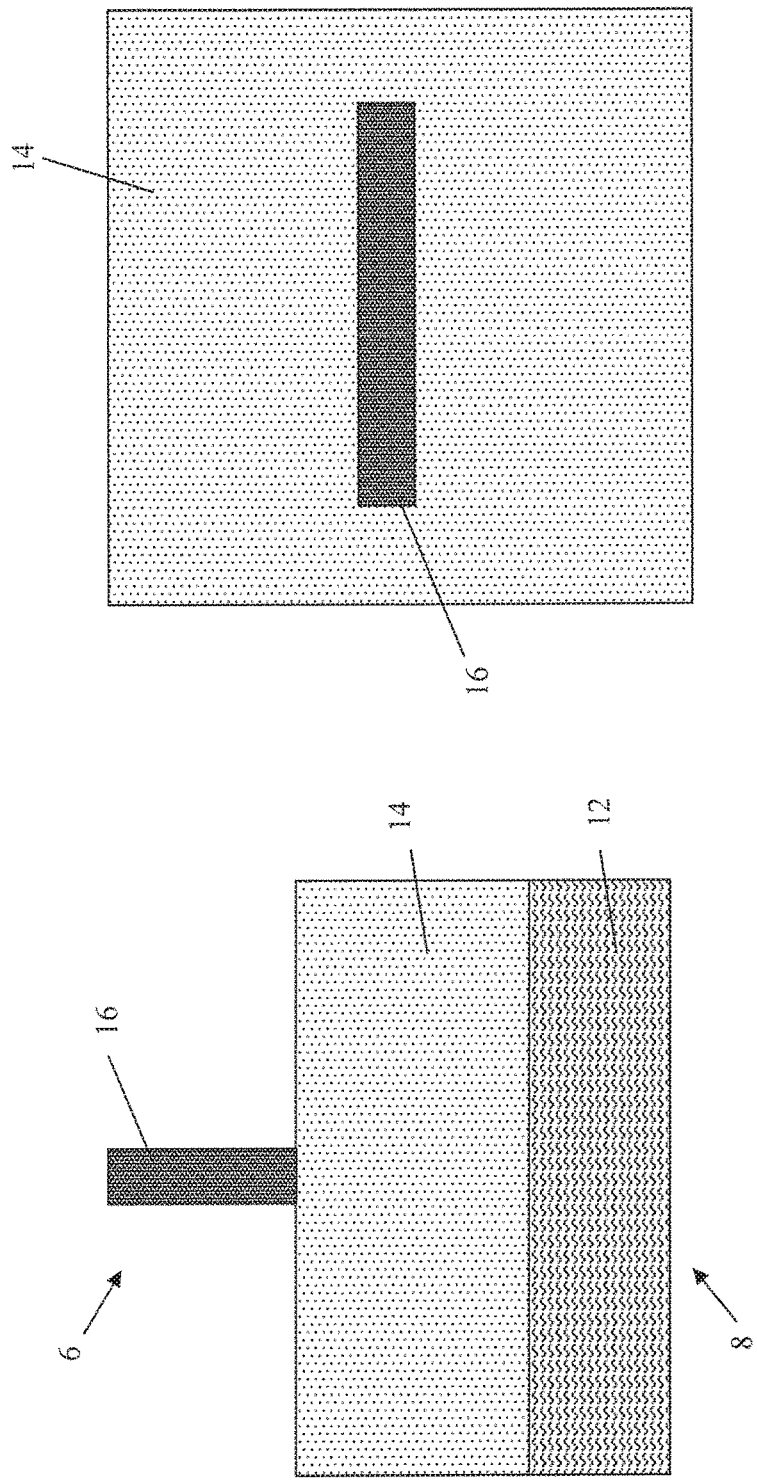

SUPERHYDROPHOBIC ELECTRODE AND BIOSENSING DEVICE USING THE SAME

BACKGROUND

Technical Field

The present invention generally relates to biosensing devices and methods, and more particularly to a superhydrophobic electrodes for detection and evaluation of molecular materials in suspension.

Description of the Related Art

Detection of ultra-low concentrations of biomolecules (e.g., DNA) is of interest for various applications in medicine, food safety and security. In highly diluted solutions, the sensor response time is limited by physical diffusion of the biomolecules to a sensor surface. One approach to overcome the diffusion limit is employing (super/ultra) hydrophobic sensor surfaces to facilitate the delivery of the biological molecules within a droplet disposed on a surface of the sensor by facilitating droplet evaporation. The approaches demonstrated to date; however, suffer from at least one or more of the following, (i) complex instrumentation, (ii) lack of scalability to small/portable sizes, (iii) non-label-free (barcode-based) detection, (iv) lack of statistical robustness due to single end-point detection, and/or (v) lack of compatibility with standard nanofabrication technology (e.g., lack of complementary metal oxide semiconductor (CMOS) technology).

SUMMARY

In accordance with an embodiment of the present invention, a method for making a hydrophobic biosensing device includes fanning alternating layers over a top and sides of a fin on a dielectric layer to form a stack of layers. The stack of layers are planarized to expose the top of the fin. The fin and every other layer are removed to form a cathode group of fins and an anode group of fins. A hydrophobic surface on the two groups of fins.

Another method for making a hydrophobic biosensing device includes forming a fin on a dielectric layer from a first material; growing a first layer of a material selectively removable relative to the fin over a top and sides of the fin; growing a second layer over the top and sides of the first layer; alternately growing first and second layers over a top and sides of a corresponding previous layer until a stack of layers is formed; planarizing the stack of layers to expose the top of the fin; selectively etching the stack of layers to remove the fin and the second layers to form two groups of fins from the first layers; forming a hydrophobic surface on the two groups of fins; and connecting electrodes to the two groups of fins to form a cathode and an anode.

A hydrophobic biosensing device includes a cathode group of fins formed on a dielectric layer from a semiconductor material and an anode group of fins formed on the dielectric layer from the semiconductor material and separated from the cathode group of fins. A hydrophobic surface is formed on the cathode group of fins and the anode group of fins. Electrodes are coupled to ends of the cathode group of fins and ends of the anode group of fins.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 1 is a cross-sectional view showing a fin formed on a substrate in accordance with an embodiment of the present invention;

FIG. 2 is a top view showing the fin of FIG. 1 formed on the substrate in accordance with an embodiment of the present invention;

DETAILED DESCRIPTION

Figure 4:
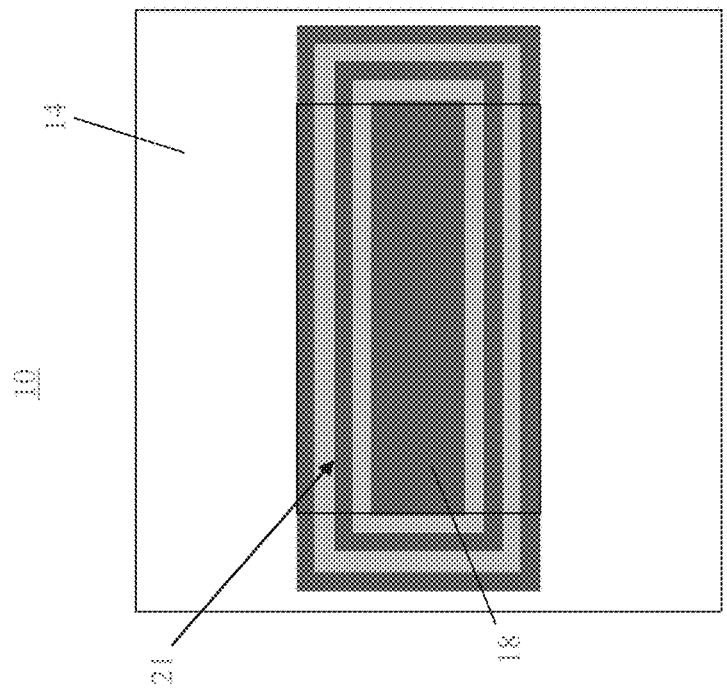
FIG. 4 is a top view showing the fin of FIG. 3 covered by layers of alternating materials in accordance with an embodiment of the present invention.

The present embodiments are directed to complementary metal oxide semiconductor (CMOS) compatible (super/ultra) hydrophobic electrode structures and fabrication methods that enable label-free detection of biological molecules via impedance spectroscopy. In accordance with useful embodiments, simple instrumentation having small size, portability and statistical robustness (e.g., by employing differential/parallel detection) is provided.

In one or more embodiments, super/ultra-hydrophobicity is achieved by a combination of intrinsic surface hydrophobicity (e.g., induced by directed self-assembly of organic monolayers) and topology of a nanostructure. In some embodiments, the topology can further include a secondary surface nanostructure (e.g., hierarchical structures). In some embodiments, the nanostructures can have a sub-lithographic pitch.

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Referring now to the drawings in which like numerals represent the same or similar elements and initially to FIG. 1, a partially fabricated structure or device 10 is shown including a substrate 8. The substrate 8 can include a bulk or base semiconductor substrate 12 having a buried dielectric layer 14 foamed or provided thereon. In one example, the bulk semiconductor substrate 12 can be a silicon-based material. Illustrative examples of Si-based materials suitable for the bulk semiconductor substrate 12 include, but are not limited to, Si, SiGe, SiGeC, SiC, polysilicon, e.g., polySi, epitaxial silicon, e.g., epi-Si, amorphous Si, e.g., α:Si, and multi-layers thereof. Although silicon is the predominately used semiconductor material in wafer (CMOS) fabrication, alternative semiconductor materials can be employed, such as, but not limited to, germanium, gallium arsenide, gallium nitride, silicon germanium, cadmium telluride, zinc selenide, etc. The semiconductor substrate 8 may also be a semiconductor on insulator (SOI) substrate. In other embodiments, a dielectric substrate 14 may be employed.

The substrate 8 includes a semiconductor layer 6. The semiconductor layer 6 can include any semiconducting material including, but not limited to Si, strained Si, SiC, SiGe, SiGeC, Si alloys, Ge, Ge alloys, GaAs, InGaAs, GaN, GaP, InGaP, InAlP, InGaAlP, AlGaAs, InAs, and InP, or any combination thereof. The semiconductor layer 6 can be patterned by employing a lithography process or other patterning process (e.g., space image transfer (SIT), etc.), and etching a fin 16 or fins into the semiconductor layer 6. The etch process may include a reactive ion etch (RIE) or other anisotropic etch or any combination thereof.

In one embodiment, the buried dielectric layer 14 is located on the semiconductor base layer 12, and the semiconductor layer 6 is located on the buried dielectric layer 14. The buried dielectric layer 14 can include an oxide, e.g., a silicon oxide, or any other suitable dielectric material or combinations of materials.

It should be understood that while a single fin is depicted, a plurality of fins can be processed in a same way to provide a multitude of locations for processing molecules. The multitude of locations can be hierarchically formed or otherwise arranged to provide organized data collection. The device 10 is compatible with CMOS processing and the substrate 8 and portions thereof may be employed in forming other components from the ones described herein. For example, transistors, capacitors, diodes, etc. can be formed.

Referring to FIG. 2, a top view of the fin 16 is shown. The top view depicts a length and width of the fin 16 on the buried dielectric layer 14. The length and width of the fin 16 can be controlled by the patterning process and are dependent on the application. For example, the type of molecule to be sensed can have an impact of the dimensions selected for the fin 16 as the fin 16 will control the dimensions of the other layers to be formed as will be apparent from the subsequent FIGS. and accompanying description.

Figure 3:
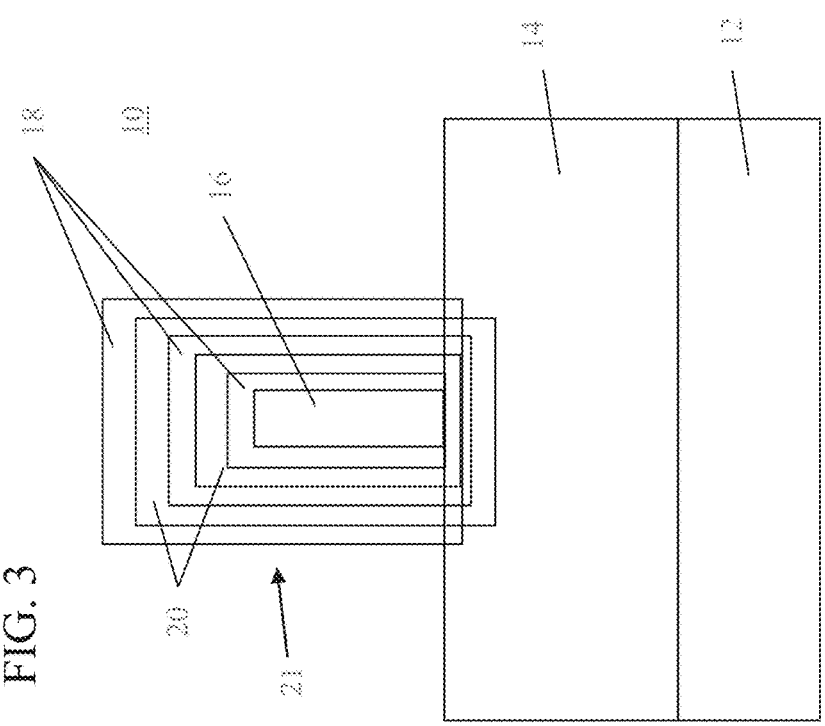
FIG. 3 is a cross-sectional view showing the fin of FIG. 1 covered by layers of alternating materials in accordance with an embodiment of the present invention.

Referring to FIG. 3, additional layers 18 and 20 are formed over the fin 16. The additional layers 18 and 20 alternate between two (or more materials). In one embodiment, the fin 16 includes a first material, and a first layer 18 includes a second material grown on the fin 16. A next layer 20 is formed on the first layer 18. The process continues with alternating layers 18 and 20 until a sufficient number of layers 18, 20 are formed.

The number of layers 18, 20 may vary depending on the application. While FIG. 3 shows two layers 20 and three layers 18, any number of layers 18, 20 may be employed. While any number of materials can be employed for a stack 21 of layers, in one useful embodiment, the fin 16 and layers 20 include SiGe and the layers 18 include Si and, in particular, in-situ doped Si. It should be understood that the present embodiments are not limited to the SiGe material systems and that any two (or more) semiconductors that can be grown epitaxially on top of each other and can be etched selectively with respect to one another can be employed. Devices can include but are not limited to III-V materials, IV materials or combinations thereof. In some examples, the following material combinations can be employed: GaN and Si, GaAs (or InGaAs) and InGaP, GaAs (or InGaAs) and InAlP, GaAs (or InGaAs) and InGaAlP, and GaAs (or InGaAs) and AlGaAs. Other materials systems are also contemplated.

Epitaxial growth is preferable to preserve the crystallinity of the semiconductor, and to permit the uniform growth of thin semiconductor layers with accurately controlled thickness; however, other growth techniques may be employed as well. Epitaxy can be performed by ultrahigh vacuum chemical vapor deposition (UHVCVD), rapid thermal chemical vapor deposition (RTCVD), metalorganic chemical vapor deposition (MOCVD), low-pressure chemical vapor deposition (LPCVD), limited reaction processing CVD (LRP-CVD), molecular beam epitaxy (MBE), etc. Epitaxial materials may be grown from gaseous or liquid precursors. Epitaxial materials may be grown using vapor-phase epitaxy (VPE), molecular-beam epitaxy (MBE), liquid-phase epitaxy (LPE), or other suitable process. Epitaxial silicon and silicon germanium (SiGe), etc. can be doped during deposition (in-situ doped) by adding dopants, n-type dopants (e.g., phosphorus or arsenic) or p-type dopants (e.g., boron or gallium), depending on the type of transistor. The dopant concentration can range from about $1 \times 10^{19}$ cm$^{-3}$ to about $2 \times 10^{21}$ cm$^{-3}$, or preferably between $2 \times 10^{20}$ cm$^{-3}$ and $1 \times 10^{21}$ cm$^{-3}$. When SiGe is epitaxially grown, the SiGe may have germanium content in the range of 5% to 80%, or preferably between 20% and 40%.

The terms "epitaxial growth and/or deposition" and "epitaxially formed and/or grown," mean the growth of a semiconductor material (crystalline material) on a deposition surface of another semiconductor material (crystalline material), in which the semiconductor material being grown (crystalline over layer) has substantially the same crystalline characteristics as the semiconductor material of the deposition surface (seed material). In an epitaxial deposition process, the chemical reactants provided by the source gases are controlled, and the system parameters are set so that the depositing atoms arrive at the deposition surface of the semiconductor with sufficient energy to move about on the surface such that the depositing atoms orient themselves to the crystal arrangement of the atoms of the deposition surface. Therefore, an epitaxially grown semiconductor material has substantially the same crystalline characteristics as the deposition surface on which the epitaxially grown material is formed.

Referring to FIG. 4, a top view of the stack 21 is shown. The top view depicts a length and width of the stack 21 over the buried dielectric layer 14. The length and width of the stack 21 can be controlled by the thickness of each constituent layer 18, 20 (FIG. 3).

Figure 6:
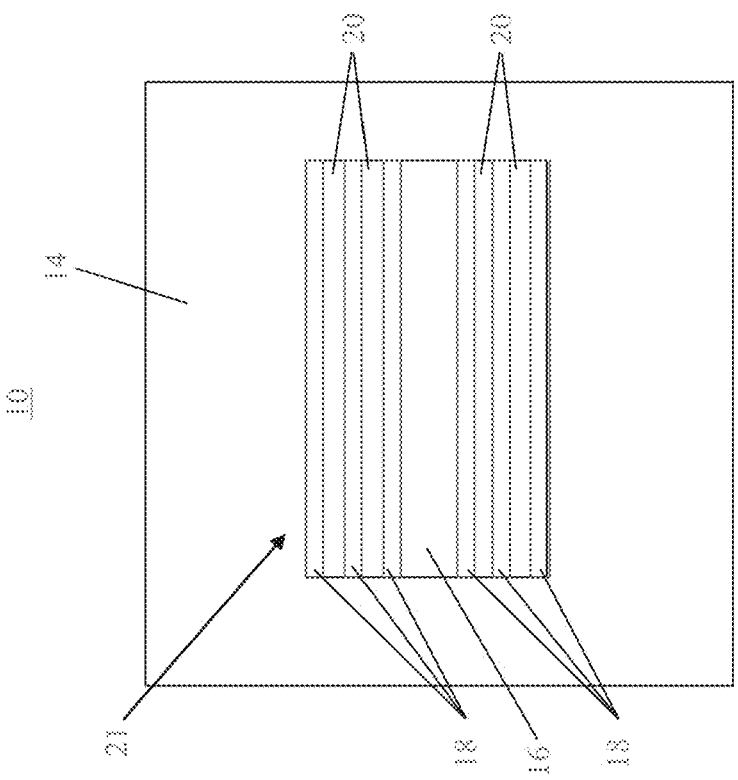
FIG. 6 is a top view showing the stack of layers of FIG. 5 in accordance with an embodiment of the present invention.
Figure 5:
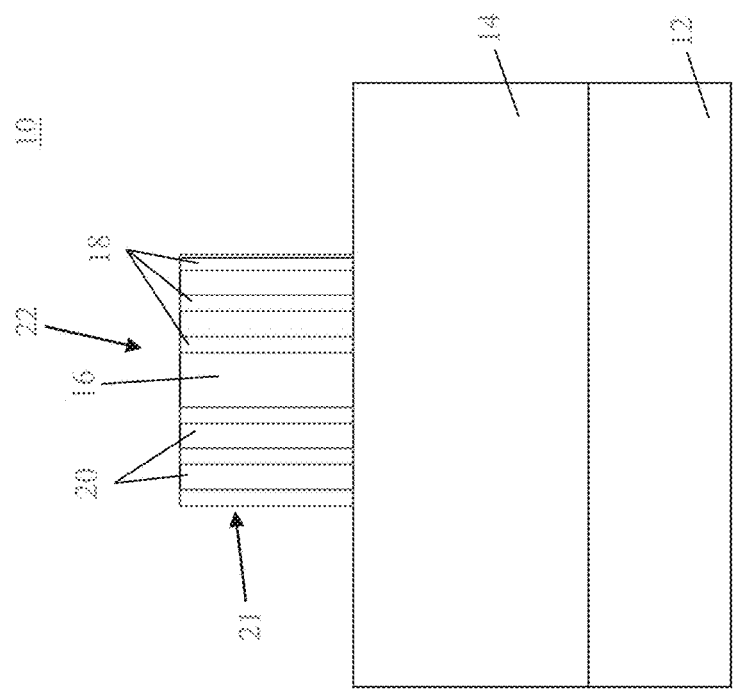
FIG. 5 is a cross-sectional view showing a stack of layers of FIG. 3 planarized to expose a core fin in accordance with an embodiment of the present invention.

Referring to FIGS. 5 and 6, a cross-sectional view (FIG. 5) and a top view (FIG. 6) are shown after a planarization process. The structure 10 of FIGS. 3 and 4 is buried in a dielectric fill material (not shown). The dielectric fill material can include an oxide or similar fill material. The dielectric fill material fills around the stack 21 or stacks. Then, a planarization process is performed to remove any dielectric fill on the top of the stack 21 and to remove a top of the stack 21 to expose a top of the fin 16 and to form a surface 22. The planarization process can include a chemical mechanical polish (CMP). The dielectric fill is then selectively removed using a selective etch process.

Figure 8:
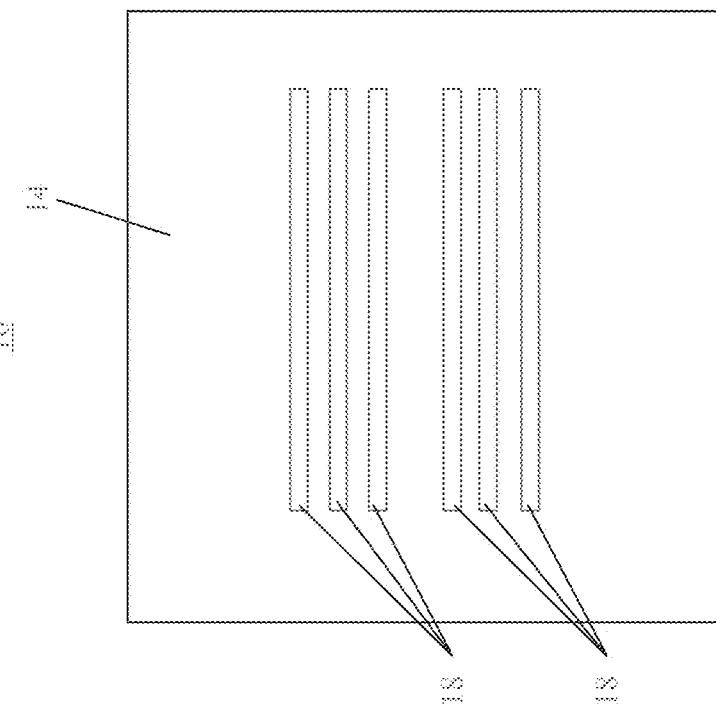
FIG. 8 is a top view showing the anode and cathode groups of fins of FIG. 7 in accordance with an embodiment of the present invention.
Figure 7:
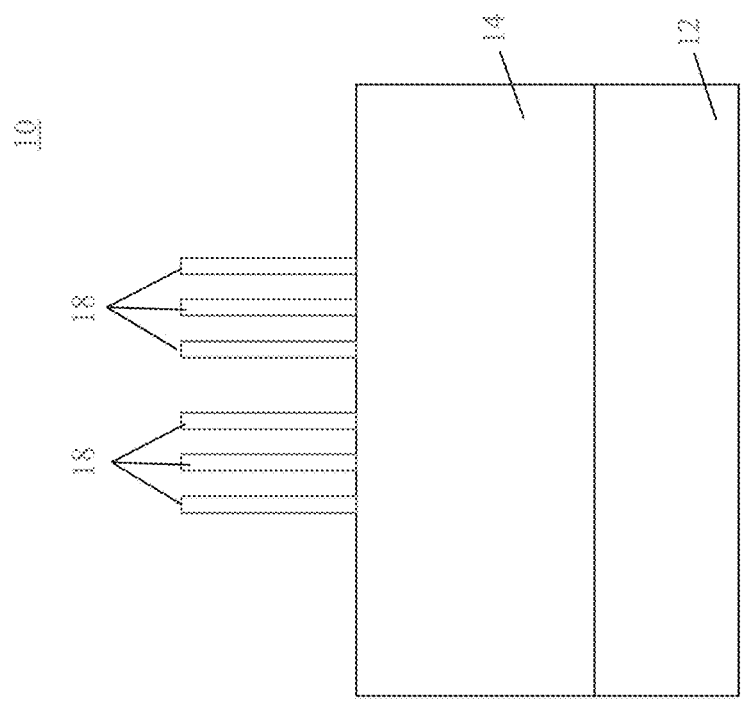
FIG. 7 is a cross-sectional view showing fins formed by selective removal of alternating layers of a common material from a stack of layers of FIG. 5 to form anode and cathode groups of fins in accordance with an embodiment of the present invention.

Referring to FIGS. 7 and 8, layers 20 and fin 16 are selectively removed relative to the layers 18 and buried dielectric layer 14. In useful embodiments, the selective etch includes a wet etch. An example of a wet etch for Ge (and/or SiGe) which is selective to Si includes a mixture of $H_3PO_4$, $CH_3COOH$, $HNO_3$ and water. Another example includes HCl and water. If other materials are employed for fins 16 and layers 18 and 20, an example of a wet etch for (In)GaAs which is selective to InGaP, InAlP, InGaAlP and AlGaAs includes a mixture of $H_2O_2$, citric acid and water. An example of a wet etch for InGaP, InAlP, InGaAlP and AlGaAs which is selective to (In)GaAs includes HCl and water.

Figure 9:
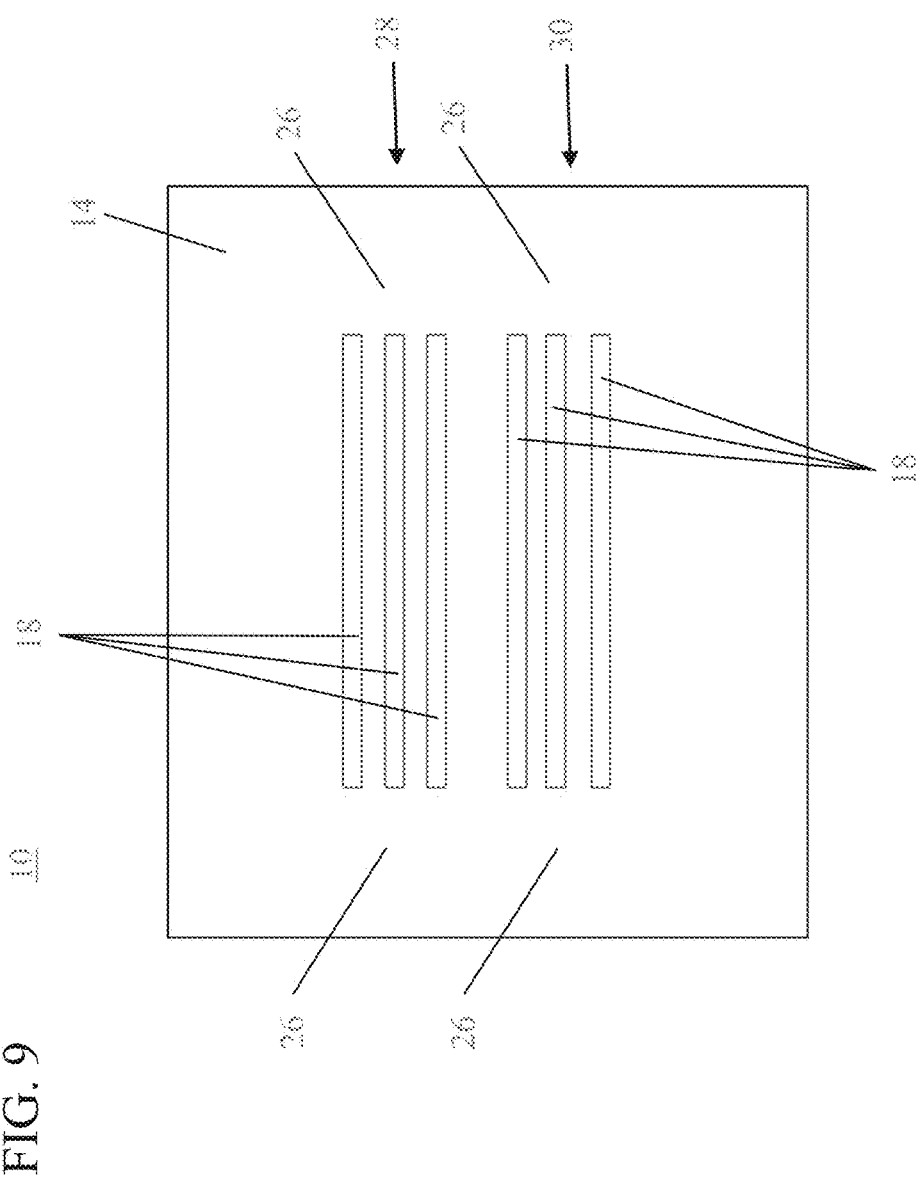
FIG. 9 is a top view showing anode and cathode groups of fins coupled to electrodes in accordance with an embodiment of the present invention.

Referring to FIG. 9, a top view shows electrodes 26 formed in contact with the layers 18. The electrodes 26 include a cathode 28 and an anode 30 (or vice versa). The electrodes 26 may be formed by masking portions of the layers 18, depositing a conductive material and patterning the conductive material to form the electrodes 26 and connections to the electrodes (e.g., conductive lines, etc.). The conductive material may be deposited using chemical vapor deposition, atomic layer deposition, sputtering, evaporation, etc.

The electrodes 26 may include any suitable conductive material, such as polycrystalline or amorphous silicon, a metal (e.g., tungsten, titanium, tantalum, ruthenium, zirconium, cobalt, copper, aluminum, lead, platinum, tin, silver, gold), a conducting metallic compound material (e.g., tantalum nitride, titanium nitride, tungsten silicide, tungsten nitride, ruthenium oxide, cobalt silicide, nickel silicide), conductive carbon or any suitable combination of these materials. The conductive material may further comprise dopants that are incorporated during or after deposition.

In one embodiment, a silicide may be formed between the layers 18 and the electrodes 26. This may include forming the electrodes from a material that can form a silicide or coating portions of the layers 18 with a material that forms a silicide (prior to forming the electrodes 26). Materials that form silicides, can include, e.g., Ti, Ni, Pt, etc. The device 10 is annealed to cause mixing of material to form silicides and improve electrical contact between layers 18 and electrodes 26.

Embodiments of the present invention may be employed using the structure 10 of FIG. 9. However, treatments and/or coatings may be provided on the layers 18 to further enhance the usefulness of the structure 10. In particularly useful embodiments, the surface of the layers 18 is made hydrophobic. The hydrophobic nature of layers 18 may be achieved mechanically, chemically or both. In one example, a CMP process can be deliberately adjusted to leave secondary nano-scale features (surface roughness) on the top surface of the layers 18 and therefore improve hydrophobicity. The treatment of the layer 18 may be performed before or after formation of the electrode 26.

It should be understood that complex circuits may be patterned along with electrodes 26 to enable hierarchical connections between different devices 10 having a same size and function or different sizes and functions as other devices on the same chip.

Figure 10:
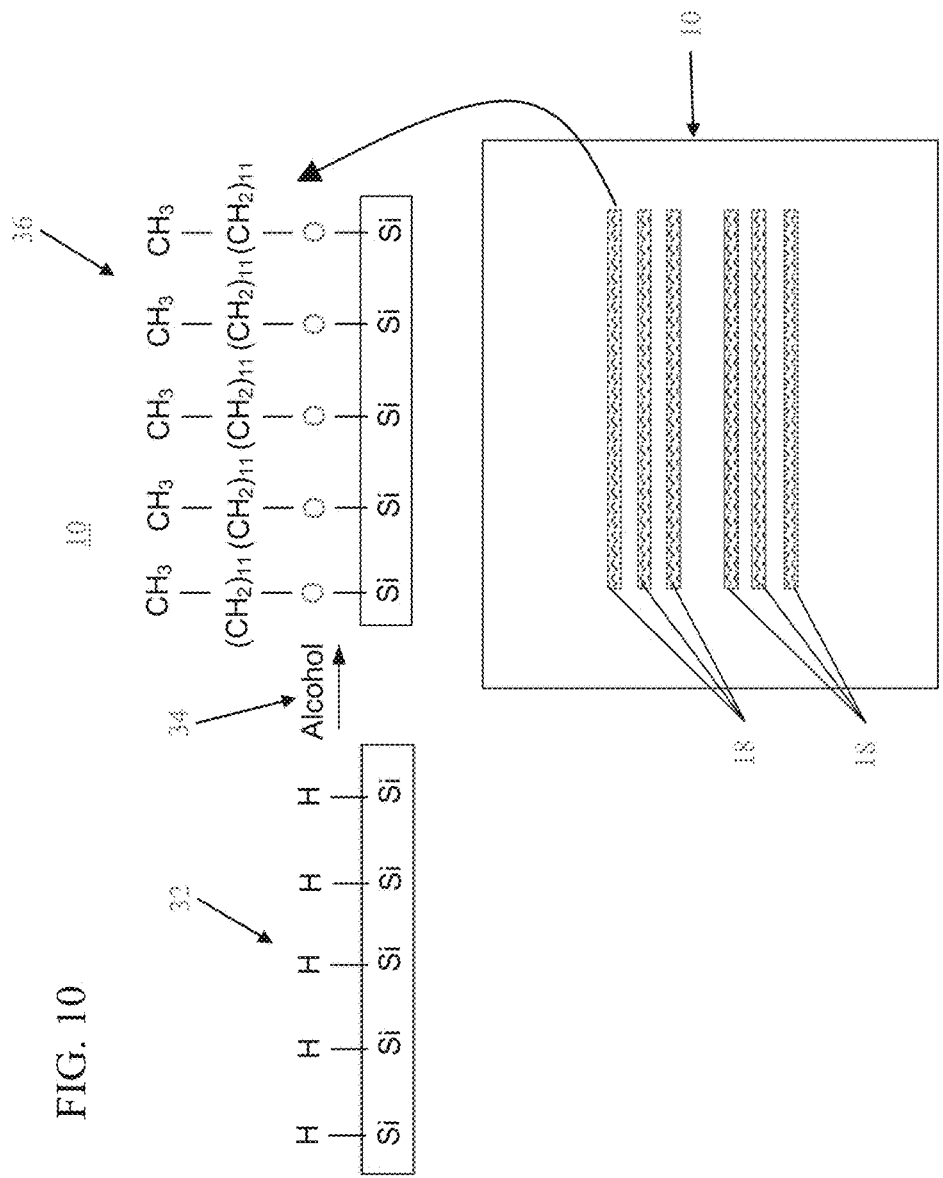
FIG. 10 is a top view showing the anode and cathode groups of fins having a hydrophobic surface formed thereon prior to forming the electrodes in accordance with an embodiment of the present invention.

Referring to FIG. 10, in one useful embodiment, layers 18 can be treated to chemically alter or coat a surface of the layers 18 to make the layers 18 hydrophobic. In one embodiment, the layers 18 are treated prior to formation of the electrodes 26 to make the layers 18 permanently hydrophobic. In one example, the surface of the layers 18 (e.g., Si) is H-terminated by performing an HF dip or other process to form an H-terminated surface 32. H termination of the Si (or other semiconductor) surface of layers 18 can be achieved by dipping the device 10 in dilute HF solution, exposing the layers 18 to H-containing plasma or radicals, etc.

Self-assembly of an organic monolayer 36 can be achieved by dipping the device 10 into a long-chain alcohol or thiol 34, in temperatures from about room-temperature to about 100° C. An example of a long-chain alcohol includes 1-dodecanol. Other alcohols can also be employed.

Figure 11:
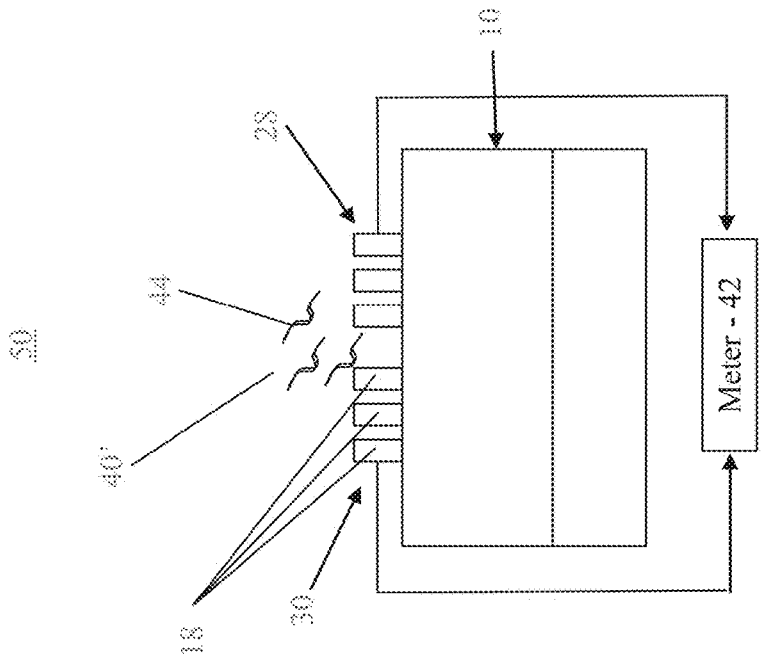
FIG. 11 is a schematic diagram showing a droplet formed on a biosensing device for measuring impedance at a first time instance in accordance with one embodiment.
Figure 12:
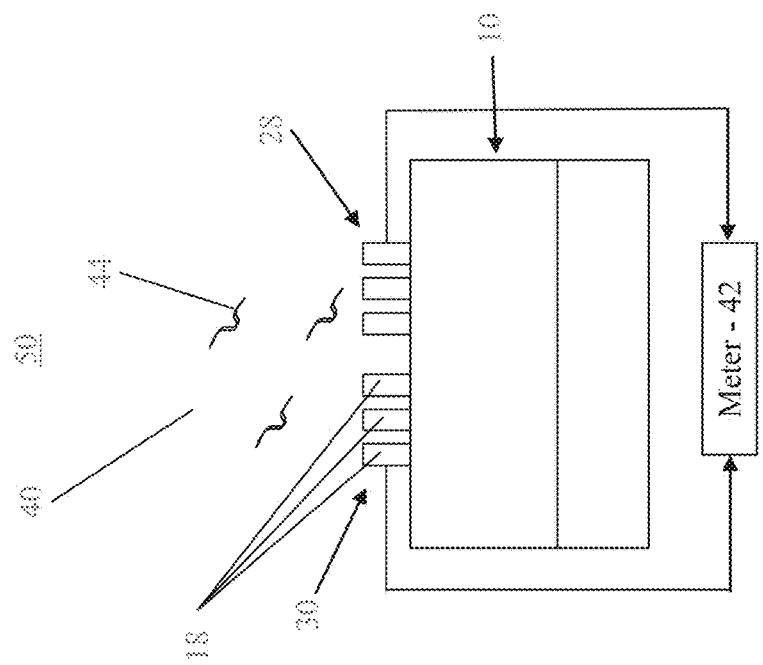
FIG. 12 is a schematic diagram showing a droplet formed on the biosensing device for measuring impedance at a second time instance after evaporation in accordance with one embodiment.

Referring to FIGS. 11 and 12, schematic diagrams show a potential application for device 50 in accordance with one embodiment. FIG. 11 shows a droplet 40 at a first time, t1, and FIG. 12 shows a droplet 40 ' (reduced by evaporation from droplet 40) at a later time, t2. Device 50 includes layers 18 formed as fins and grouped into a cathode 28 and anode 30. The fins or layers 18 are surfaced to be hydrophobic. The droplet 40 is placed over the cathode 28 and anode 30. The droplet includes bio-molecules 44, such as DNA, RNA, viruses, bacteria, or other molecules.

The cathode 28 and the anode 30 are coupled to an impedance measurement system or meter 42, such as, e.g., an inductance, capacitance, resistance (LCR) meter. An impedance can be measured using the meter 42.

The impedance measurement system 42 measures the droplet 40 at time t1, and measures an impedance measurement of the same droplet 40' at a later time t2 (FIG. 12). Over time, droplet evaporation results in an increase in concentration of the molecules 44 (e.g., DNA) in solution, which consequently leads to an increase in the solution conductance (e.g., a decrease in the impedance magnitude). A volume of the elongated droplet 40 decreases as it evaporates, however, its contact line (and its contact area) does not change, as the line is held by surface tension of the drop 40 or 40' and the hydrophobic surface on the layers 18. An invariance of this contact area makes the impedance measurements more robust and reliable. If the droplet contact line changes with time, the loss of the area-coverage would increase the electrode impedance in an uncontrolled manner. With a fixed contact area, the increase in the DNA concentration (or other molecule) with electrolyte evaporation (deionized (DI) water) or the droplet 40, 40'is accurately reflected in a decrease of the droplet impedance as a function of time.

Figure 13:
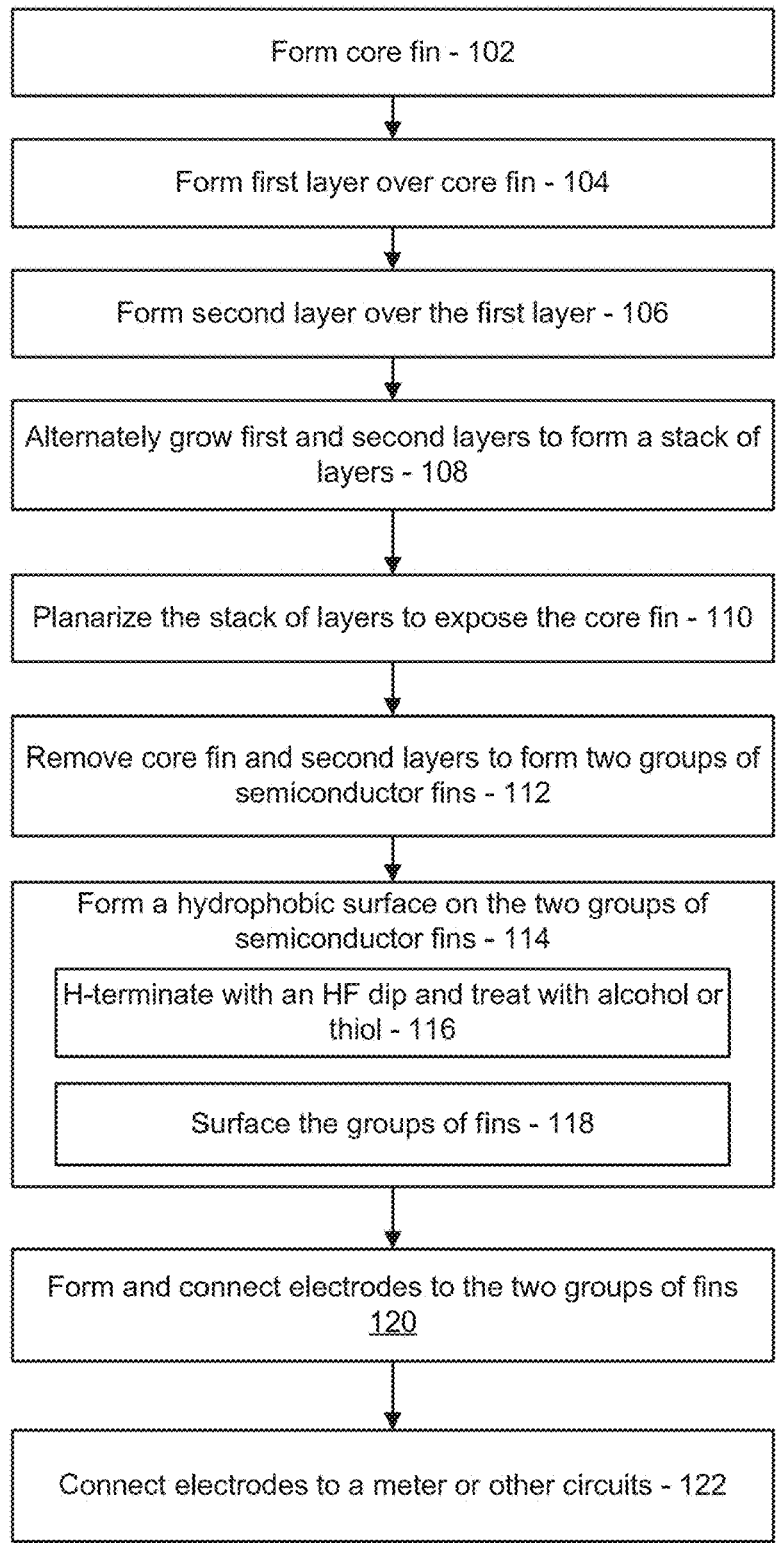
FIG. 13 is a block/flow diagram showing a system/method for fabricating a biosensing device in accordance with embodiments of the present invention.

Referring to FIG. 13, methods for making a hydrophobic biosensing device are illustratively shown. In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In block 102, a core fin (or fins) are formed on a dielectric layer from a first material. The core fin includes a width employed to form a gap between a cathode and an anode as will be described.

In block 104, a first layer of a material that is selectively removable relative to the fin is formed over a top and sides of the fin. In block 106, a second layer is grown over the top and sides of the first layer. In block 108, first and second layers are alternately grown over a top and sides of a corresponding previous layer until a stack of layers is formed.

In block 110, the stack of layers is planarized to expose the top of the core fin. In one embodiment, a dielectric fill can be formed prior to planarization, and removed after planarization. In block 112, the stack of layers are selectively etched to remove the core fin and the second layers to form two groups of semiconductor fins formed from the first layers. The groups of fins can be separated by the width of the core fin. The two groups of fins can include doped Si or a doped III-V material.

In block 114, a hydrophobic surface is formed on the two groups of fins. In block 116, the hydrophobic surface can be formed by hydrogen terminating a surface of the two groups of fins and treating a hydrogen-terminated surface of the two groups of fins with an alcohol or thiol. The hydrogen terminated surface may be formed by dipping the surface in HF. In one example, the alcohol may include 1-dodecanol. The surface preparation can be permanent and provides a superhydrophobic surface. In block 118, the hydrophobic surface can be formed or further enhanced by surfacing the groups of fins, e.g., roughening the surface or polishing.

In block 120, electrodes are formed and connected to the two groups of fins to form a cathode and an anode. In block 122, the electrodes can be connected to a meter to measure droplets applied to the anode and cathode.

Having described preferred embodiments superhydrophobic electrode and biosensing device using the same (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for making a hydrophobic biosensing device, comprising:
    forming alternating vertically oriented layers on sides of a fin on a dielectric layer;
    removing the fin and every other vertically oriented layer to form a cathode group of fins and an anode group of fins; and
    forming a hydrophobic surface on the two groups of fins.

2. The method as recited in claim 1, further comprising connecting electrodes to the two groups of fins.

3. The method as recited in claim 1, wherein forming the hydrophobic surface includes:
    hydrogen terminating a surface of the two groups of fins; and
    treating a hydrogen-terminated surface of the two groups of fins with an alcohol or thiol.

4. The method as recited in claim 1, wherein the fin includes a width that forms a gap between the cathode group of fins and the anode group of fins.

5. The method as recited in claim 1, wherein the hydrophobic surface comprises an organic monolayer.

6. The method as recited in claim 1, wherein the cathode group of fins and the anode group of fins include at least one of a doped III-V material or doped Si.

7. The method as recited in claim 3, wherein hydrogen terminating the surface includes dipping the surface in HF.

8. The method as recited in claim 3, wherein the alcohol includes 1-dodecanol.

9. A method for making a hydrophobic biosensing device, comprising:
    alternately growing first and second layers over a top and sides of a corresponding previous layer until a stack of layers is formed over a top and sides of a fin;
    selectively removing the stack of layers to remove the fin and the second layers to form two groups of fins from the first layers;
    patterning a conductive layer on the two groups of fins;
    forming a hydrophobic surface on the two groups of tins; and
    connecting electrodes to the two groups of fins to form a cathode and an anode.

10. The method as recited in claim 9, wherein forming the hydrophobic surface includes:
    hydrogen terminating a surface of the two groups of fins; and
    treating a hydrogen-terminated surface of the two groups of fins with an alcohol.

11. The method as recited in claim 9, wherein the fin includes a width that forms a gap between the cathode and the anode.

12. The method as recited in claim 9, wherein the hydrophobic surface comprises an organic monolayer.

13. The method as recited in claim 9, wherein the two groups of fins include at least one of a doped III-V material or doped Si.

14. The method as recited in claim 10, wherein hydrogen terminating the surface includes dipping the surface in HF.

15. The method as recited in claim 10, wherein the alcohol includes 1-dodecanol.

16. A hydrophobic biosensing device, comprising:
    a first group of fins formed on a dielectric layer from a semiconductor material;
    a second group of fins formed on the dielectric layer from the semiconductor material and separated from the first group of fins; and
    a hydrophobic surface comprising an organic monolayer formed on the first group of fins and the second group of fins.

17. The device as recited in claim 16, wherein the hydrophobic surface includes a long-chain alcohol or thiol reacted to the surface.

18. The device as recited in claim 16, wherein the fin includes a width that forms a gap between the first group of fins and the second group of fins.

19. The device as recited in claim 16, wherein the first group of fins and the second group of fins include at least one of a doped III-V material or doped Si.

20. The device as recited in claim 17, wherein the long-chain alcohol includes 1-dodecanol.

* * * * *